United States Patent [19]

Gaffar

[11] 4,436,721
[45] Mar. 13, 1984

[54] ORAL COMPOSITION HAVING MOLE RATIO OF TETRA (METHYLENE PHOSPHONATE) TO ALKALI METAL FLUORIDE OF AT LEAST 1.4:1

[75] Inventor: Abdul Gaffar, Somerset, N.J.

[73] Assignee: Colgate-Palmolive Company, New York, N.Y.

[21] Appl. No.: 502,078

[22] Filed: Jun. 8, 1983

[51] Int. Cl.$^3$ .................... A61K 7/16; A61K 7/18; A61K 7/22

[52] U.S. Cl. .................................. 424/52; 424/49; 424/34

[58] Field of Search ................................ 424/52

[56] References Cited

U.S. PATENT DOCUMENTS

| | | | |
|---|---|---|---|
| 4,137,303 | 1/1979 | Gaffar et al. | 424/52 |
| 4,143,128 | 3/1979 | Kim et al. | 424/54 |
| 4,177,258 | 12/1979 | Gaffar et al. | 424/52 |
| 4,183,915 | 1/1980 | Gaffar et al. | 424/52 |

FOREIGN PATENT DOCUMENTS 2224516 12/1973 Fed. Rep. of Germany .

OTHER PUBLICATIONS

Chem. Abstr. 80:74327k, (1974) of Ger. Offen. 2224516, (12-06-73) (Counterpart of Henkel & CIE British Patent No. 1,394,034.
Chem. Abstr. 92:135445a, (1980), of U.S. 4,177,258, (12-04-79).
Chem. Abstr. 99:64269w, (1983), Calcif. Tissue Int. 35:362-365, (1983), Effects of Editempa on Dental Calculus and Caries Formation in vivo.

*Primary Examiner*—Shep K. Rose
*Attorney, Agent, or Firm*—Robert L. Stone; Murray M. Grill; Herbert S. Sylvester

[57] ABSTRACT

Anti-caries, anti-calculus oral composition, such as dental cream or gel or mouthwash, containing a diamine tetra (methylene phosphonic acid) salt, such as ethylene diamine tetra (methylene polyphosphonic acid) salt, and alkali metal fluoride, such as sodium fluoride. The mole ratio of the tetra (methylene phosphonate) portion to fluoride is at least 1.4:1, thereby providing optimum anti-caries and anti-calculus effects.

8 Claims, No Drawings

ORAL COMPOSITION HAVING MOLE RATIO OF TETRA (METHYLENE PHOSPHONATE) TO ALKALI METAL FLUORIDE OF AT LEAST 1.4:1

This invention relates to an oral composition. In particular, it relates to an anti-caries, anti-calculus oral composition in which each of the anti-caries agent and the anti-calculus agent does not substantially reduce the effect of the other. In other words, the oral composition of the invention possesses optimum anti-caries and anti-calculus effectiveness.

Diamine tetra (methylene phosphonates), such as ethylene diamine tetra (methylene phosphonates), are recognized as effective anti-calculus agents in oral compositions. These materials inhibit nucleation of calcium and phosphate materials in saliva environment of the oral cavity to form hydroxyapatite, the principal component of calculus. They are disclosed as anti-nucleating agents and calculus inhibitors in U.S. Pat. No. 4,143,128 to Kim et al; U.S. Pat. No. 4,137,303 to Gaffar et al; U.S. Pat. No. 4,177,258 to Gaffar et al; U.S. Pat. No. 4,183,915 to Gaffar et al; and British Pat. No. 1,394,034 to Henkel.

In these disclosures, except for U.S. Pat. No. 4,143,128, it is indicated that a fluoride source may be present. Fluoride sources are well known anti-caries agents. The prior art leaves great latitude to the skilled worker in the art as to the amounts of diamine poly (methylene phosphonate) and fluoride source as well as the type of fluoride source.

However, it has been observed that with various fluoride sources and various mol ratios of tetra (methylene phosphonate) to fluoride, although the anti-caries effect may be maintained, the anti-nucleation, calculus inhibition effect is diminished. Thus, when the fluoride source is sodium monofluorophosphate, stannous fluoride or amine fluoride, such as N,N',N'-hydroxy N-ocetadecyl 1,3-amino propane hydrofluoride, calculus inhibition by diamine tetra (methylene phosphonate) is reduced. Moreover, when the fluoride source is alkali metal fluoride, e.g. sodium fluoride, unless a particular mol ratio of tetra (methylene phosphonate) to fluoride is maintained, calculus inhibition is also diminished.

The mol ratio of tetra (methylene phosphonate), that is $(CH_2-PO_3^{-2})_4$ (m. Wt. 372), to fluoride (M. Wt. 19) found to be optimum in accordance with the invention is at least about 1.4:1. In the toothpaste example in British Pat. No. 1,394,034 to Henkel, 2.0 parts by weight of a substituted ethylene diamine-bis (methylene phosphonic acid) was used with 0.5 parts by weight of sodium monofluorophosphate, which corresponds to a mole ratio of tetra (methylene phosphonate) to fluoride of about 1.56:1. Sodium monofluorophosphate, however, even in this mol ratio with regard to diamine tetra (methylene phosphonate) does not avoid reduction of the anti-calculus effect and thus does not suggest that a different source could achieve this end.

It is an advantage of this invention that an oral composition is provided with optimum anti-caries and anti-calculus effect.

Other advantages will be apparent from consideration of the following disclosure.

In accordance with certain of its aspects, this invention relates to an oral composition comprising an oral vehicle, at least about 0.275% by weight of a dimaine tetra (methylene phosphonate) having the formula:

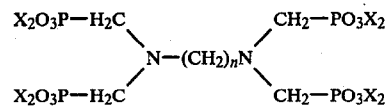

wherein n in a number from 1 to 10 and X is selected from the group consisting of hydrogen and an orally acceptable cation, at least one X group being an orally acceptable cation, and alkali metal fluoride, in amount which provides about 0.01–1% by weight of fluoride ion, the mole ratio of tetra (methylene phosphonate) portion, $(CH_2-PO_3^{-2})_4$, to fluoride ion being at least about 1.4:1.

The diamine tetra (methylene phosphonate) compounds which are preferred are those in which the n group is 2 to 8 and those which are most preferred are pharmaceutically acceptable salts of ethylenediamine tetra (methylenephosphonic acid), (hereinafter EDITEMPA), (e.g. sodium, potassium, and ammonium and other pharmaceutically acceptable salts; most preferably the tri-, tetra-, penta-, hexa- or hepta sodium salts). Other diamine tetra (methylene phosphonate) compounds include the salts of tetramethylenediamine tetra (methylene phosphonic acid), pentamethylene diamine tetra (methylenephosphonic acid), hexamethylene diamine tetra (methylene phosphonic acid) and octamethylenediamine tetra (methylene phosphonic acid).

Mixtures of any of the diamine tetra (methylene phosphonates) can be used in the practice of this invention. The diamine tetra(methylene phosphonates) can be prepared in any convenient manner, for example, according to the teachings of U.S. Pat. No. 3,928,956 or Moedritzer and Irani, Journal or Organic Chemistry, May, 1966, pages 1603–1607.

The concentration of diamine tetra (methylene phosphonates) in the oral compositions can range widely, so long as the mol ratio of the tetra (methylene phosphonate) portion to fluoride ion is at least about 1.4:1. The upper amount may also be based on the amount of fluoride ion. Generally, concentrations from about 0.275% to about 5.5% by weight are utilized. The mole ratio of tetra (methylene phosphonate) to fluoride may vary from about 1.4:1 to about 3.2:1 or more.

Alkali metal fluorides, such as sodium fluoride, potassium fluoride, lithium fluoride and ammonium fluoride have been disclosed as effective fluoride-providing anti-caries agents. Indeed, they have been disclosed for this purpose since the early development of oral compositions containing fluorides; for instance in U.S. Pat. No. 2,876,166 to Nebergall, U.S. Pat. No. 2,876,167 to Manahan and U.S. Pat. No. 3,227,617 to Manahan et al. It is desirable to use alkali metal fluorides in oral compositions in anti-caries effective, non-toxic fluoride amounts, such as about 0.1–1% by weight, preferably about 0.045–0.15%, based on fluoride ion. Sodium fluoride is preferred, typically in amount of compound of about 0.022–2.2% by weight, preferably about 0.1–0.32%.

In certain highly preferred forms of the invention the oral composition may be substantially liquid in character, such as a mouthwash or rinse. In such a preparation the vehicle is typically a water-non-toxic-alcohol mixture. Generally, the ratio of water to alcohol, e.g. ethanol, is in the range of from about 1:1 to about 20:1 preferably from 3:1 to 20:1 and most preferably about 5:1 to 6:1, by weight. The total amount of water-alcohol mixture in this type of preparation is typically in the range of from about 70% to about 99.9% by weight of the preparation. The pH of such liquid preparations is generally in the range of from about 4.5 to about 9 and typically from about 5.5 to 8. The pH is preferably in the range of from about 6 to 7.5. The pH may be adjusted, if desired, e.g. with sodium hydroxide. It is noteworthy that the composition of the invention permits the use of diamine tetra (methylene phosphonate) at a pH below 5 without substantially decalcifying dental enamel.

In certain other desirable forms of this invention, the oral composition may be substantially solid or pasty in character, such as a toothpowder, a dental tablet or a toothpaste or dental cream or gel. The vehicle of such solid or pasty oral preparations contains an orally acceptable dental polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicate, silica, bentonite, melamine formaldehyde, urea formaldehyde, polyacrylates, and mixtures thereof. Preferred polishing materials include siliceous polishing agents, e.g. crystalline silica having particle sizes of up to 5 microns, a mean particle size of up to 1.1 microns, and a surface area of up to 50,000 cm$^2$/gm. silica hydrogel, xerogel, complex amorphorous alkali metala aluminosilicate (silica containing combined alumina).

When visually clear gels are employed, a polishing agent of colloidal silica, such as those sold under the trademark SYLOID as Syloid 72 and Syloid 74 or under the trademark SANTOCEL as Santocel 100 and complexes of silica containing combined alumina are particularly useful, since they have refractive indices close to the refractive indices of gelling agent-liquid (including water and humectant) systems commonly used in dentifrices. They are also desirable in opacified creams or gels. Siliceous polishing agents are particularly preferred in view of the high compatibility with the alkali metal fluoride; that is, they permit high levels of retention of fluoride ion.

The polishing material is generally present in amounts ranging from about 15% to about 99% by weight of the oral preparation. Preferably, it is present in amounts ranging from about 15% to about 75% in toothpaste, and from about 70% to about 99% in toothpowder.

In pasty oral preparations the diamine tetra (methylene phosphonate) compound should be compatible with the other components of the preparation. Thus, in a toothpaste, the liquid vehicle may comprise water and humectant typically in an amount ranging from about 10% to about 90% by weight of the preparation. Glycerine, sorbitol, or polyethylene glycol may be present as humectants. Particularly advantageous liquid ingredients comprise mixtures of water, glycerine and sorbitol.

In clear gels, where the refractive index is an important consideration, about 3–30% by weight of water, 0 to about 80% by weight of glycerine, and about 20–80% by weight of sorbitol are preferably employed.

A gelling agent, such as natural or synthetic gums or gumlike materials, typically Irish moss, sodium carboxymethylcellulose, methyl cellulose or hydroxyethyl cellulose may be employed. Other gelling agents which may be employed include gum tragacanth and starch. They are usually present in toothpaste in an amount up to 10% by weight, preferably in the range of from about 0.5% to about 5%. The preferred gelling agents are sodium carboxymethyl cellulose, methyl cellulose and hydroxyethyl cellulose. In a toothpaste or gel, the liquids and solids are proportioned to form a creamy or gelled mass which is extrudable from a pressurized container or from a collapsible, e.g. lined aluminum or plastic, tube.

The solid or pasty oral preparation typically has a pH measured on a 20% slurry of about 4.5 to about 9, generally about 5.5 to about 8 and preferably about 6 to about 7.5.

It will be understood that, as is conventional, the oral preparations are to be sold or otherwise distributed in suitably labelled packages. Thus a jar of mouthrinse will have a label describing it, in substance, as a mouthrinse or mouthwash and having directions for its use; and a toothpaste will usually be in a collapsible tube, typically lined aluminum or plastic, or other dispenser for metering out the contents, having a label describing it, in substance, as a toothpaste or dental cream.

Organic surface-active agents may be used in the compositions of the present invention to achieve increased prophylactic action, assist in achieving thorough and complete dispersion of the instant compositions throughout the oral cavity, and render the instant compositions more cosmetically acceptable. The organic surface-active material may be anionic, nonionic, or ampholytic in nature, and it is preferred to employ as the surface-active agent a detersive material which imparts to the composition detersive and foaming properties. Suitable such detergents are water-soluble salts of higher fatty acid monoglyceride monosulfates, such as sodium lauryl sulfate, alkyl aryl sulfonates, such as sodium dodecyl benzene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl groups and the like. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide (available under the trademark ("Pluronic") and amphoteric agents such as (alkyl) amido-alkylene-alkylated amine derivative which are available under the trademark "Miranol" such as Miranol C$_2$M. It is preferred to use from about 0.05 to 5% by weight of the foregoing surface-active materials in the instant oral compositions.

Various other materials may be incorporated in the oral compositions of this invention. Examples thereof are coloring or whitening agents, preservatives, silicones, chlorophyll compounds and ammoniated materials such as urea, diammonium phosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzyhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyl-dimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavoring or sweetening materials may be employed in formulating a flavor for the compositions of the present invention. Examples of suitable flavoring constituents, include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include xylitol sucrose, lactose, maltose, sorbitol, sodium cyclamate, sodium saccharine and oxathiazin salts of U.S. Pat. No. 3,932,606. Suitably, flavor and sweetening agent may together comprise from about 0.01 to 5% or more of the instant invention.

The compositions of the invention are prepared by adding the diamine tetra (methylene phosphonate) after the fluoride is blended into the oral vehicle. For instance, in a mouthwash, alkali metal fluoride is typically dissolved in an aqueous humectant alcohol vehicle followed by addition of the diamine tetra (methylene phosphonate). In a dental cream polishing agent and alkali metal fluoride are typically dispersed in an oral vehicle pre-mix of gelling agent with humectant and water, followed by addition of the diamine tetra (methylene phosphonate).

The following specific examples are further illustrative of the nature of the present invention, but it is to be understood that the invention is not limited thereto. The compositions are prepared in the usual manner and all amounts of the various ingredients are by weight unless otherwise specified.

EXAMPLE 1

Dental creams are prepared by blending gelling agent with a premix of water and 25% of the humectant to which stabilizer and sweetener have been added to obtain a cream consistency. Thereafter polishing agent, surface active agent and fluoride are incorporated into the cream followed by the diamine tetra (methylene phosphonate) and then a blend of the remainder of the humectant and the flavor.

The dental creams have the following formulas:

| | PARTS | | | | | | |
|---|---|---|---|---|---|---|---|
| | A | B | C | D | E | F | G |
| Glycerine | 25.0 | 25.0 | 25.0 | 25.0 | 25.0 | 25.0 | 25.0 |
| Sodium carboxymethyl cellulose | 1.3 | 1.3 | 1.3 | 1.3 | 1.3 | 1.3 | 1.3 |
| Sodium benzoate | 0.5 | 0.5 | 0.5 | 0.5 | 0.5 | 0.5 | 0.5 |
| Sodium saccharin | 0.2 | 0.2 | 0.2 | 0.2 | 0.2 | 0.2 | 0.2 |
| Water | 40.1 | 37.88 | 37.88 | 37.69 | 37.58 | 38.99 | 38.99 |
| Sodium fluoride | — | 0.22 | — | 0.22 | 0.32 | 0.22 | 0.22 |
| Silica containing combined alumina (Zeo 49) | 30.0 | 30.0 | 27.0 | 27.0 | 27.0 | 29.0 | 30.0 |
| Titanium dioxide | 0.4 | 0.4 | 0.4 | 0.4 | 0.4 | 0.4 | 0.4 |
| Sodium lauryl sulfate | 1.5 | 1.5 | 1.5 | 1.5 | 1.5 | 1.5 | 1.5 |
| Flavor | 1.0 | 1.0 | 1.0 | 1.0 | 1.0 | 1.0 | 1.0 |
| 50% Sodium hydroxide | — | — | 2.47 | 2.44 | 2.45 | 0.89 | 0.44 |
| EDITEMPA | — | — | 2.75 | 2.75 | 2.75 | 1.00 | 0.50 |

EDITEMPA-sodium (6-7) salt is formed in situ.

In formulations D-G the mole ratios of the tetra (methylene phosphonate) portion to fluoride are as follows:

| Dental Gel | Mole Ratio Polyamine Polyphosphonate |
|---|---|
| D | 1.4:1 |
| E | 0.97:1 |
| F | 0.51:1 |
| G | 0.25:1 |

Calulus reductions effected by each of dental gels A-G are determined as follows:

The animals used are 70, pure bred beagle dogs, two or three years old, in good health and not having received any prior dental treatment.

The calculus formation is assessed on teeth; $P^4$, $P^3$, $P^2$, $C,I^1$ and $P_4,P_3,P_2C,I_1$ and the left and right sides, and stratified on the basis of the initial scoring into seven treatment groups.

Calculus is assessed on the scale of 0 to 3 after drying teeth with air.

0 = No calcified deposit.
1 = Calcified deposit covering less than ⅓ of the tooth surface.
2 = Calcified deposit covering more than ⅓ but less than ⅔ of tooth surface.
3 = Calcified deposit covering the entire tooth surface.

The dogs are anesthetized and receive complete dental prophylaxis, performed by two dental hygienists; that is, removal by scaling of hard and calcified deposits on the surfaces of teeth followed by polishing with pumice (Mynol) and rubber cups. A disclosing solution is used to insure the complete removal of soft and hard dental deposits.

All animals are treated twice daily, five days per week during the first nine weeks, and once daily, five days per week during the next three weeks, with the assigned dental creams provided by using 1-1.5 grams of the dental cream for each dog. A new toothbrush is used for each test material each week. Individual brushing time is approximately 30 seconds at each treatment.

The animals used in the conduct of this project are maintained in cages with welded rod bottoms, suspended over flush chutes, two animals per cage. Potable water is available ad lib and a wet, powdered Purina Dog Chow is fed once a day mixed with water to form a thick paste consistency.

The following mean calculus levels are determined after 12 weeks (including standard deviations):

| Dental Cream | Mean Calculus Level Per Tooth |
|---|---|
| A (Placebo) | 0.35 ± 0.06 |
| B (Fluoride Placebo) | 0.33 ± 0.08 |
| C (EDITEMPA Placebo) | 0.20 ± 0.12 |
| D | 0.21 ± 0.10 |
| E | 0.30 ± 0.15 |
| F | 0.43 ± 0.15 |
| G | 0.41 ± 0.15 |

Compared to the Placebo A, non-fluoride EDITEMPA Placebo dental cream C effects a significant (95%) reduction in calculus formation of 42.8% and dental cream D in which the mole ratio of tetra (methylene phosphonate) to fluoride is 1.4:1 is essentially equivalent thereto and effects a significant (95%) reduction in calculus formation of 40.0%. On the other hand, when the mole ratio of tetra (methylene phosphonate) to fluoride is lower, calculus reduction is less, being 14.2% and non-significant (95%) for dental cream E and actually permitting more calculus formation than the placebos A and B with dental creams F and G.

Upon aging for 6 weeks at 49° C., placebo dental cream reveals 930 ppm of fluoride retention (initial level-1000 ppm) and dental cream D reveals 960 ppm of fluoride retention (initial level-1000 ppm) thereby evidencing satisfactory retention of fluoride when the diamine tetra (methylene phosphonate) is present.

EXAMPLE 2

The following dental creams are prepared in accordance with the procedure outlined in Example 1:

| | PARTS | | | | |
|---|---|---|---|---|---|
| | A | B | C | D | E |
| EDITEMPA-sodium (6-7) salt | 2.75 | 2.75 | 2.00 | 2.00 | 2.75 |
| Sodium fluoride | 0.22 | — | 0.15 | — | — |
| Sodium monofluorophosphate | — | 0.76 | — | 0.50 | 0.50 |
| Sodium benzoate | 0.50 | 0.50 | 0.50 | 0.50 | 0.50 |
| Sodium saccharin | 0.20 | 0.20 | 0.20 | 0.20 | 0.20 |
| Sodium carboxymethyl cellulose | 1.40 | 1.40 | 1.40 | 1.40 | 1.40 |
| Glycerine | 25.00 | 25.00 | 25.00 | 25.00 | 25.00 |
| Silica containing combined alumina (Zeo 49) | 30.00 | 30.00 | 30.00 | 30.00 | 30.00 |
| Sodium lauryl sulfate | 1.50 | 1.50 | 1.50 | 1.50 | 1.50 |
| Flavor | 1.00 | 1.00 | 1.00 | 1.00 | 1.00 |
| Water | Q.S. TO 100 | Q.S. TO 100 | Q.S. TO 100 | Q.S. TO 100 | Q.S. TO 100 |

The mole ratio of tetra (methylene phosphonate) to fluoride in dental creams A–D is as follows:

| | Mole Ratio Polyamine Polyphonate:Fluoride |
|---|---|
| A (Sodium fluoride) | 1.4:1 |
| B (Sodium monofluorophosphate) | 1.4:1 |
| C (Sodium fluoride) | 1.5:1 |
| D (Sodium monofluorophosphate) | 1.5:1 |

The bioavailability of each of dental creams A–D is compared to non-fluoride placebo dental cream E by the following procedure:

20 grams of hydroxyapatite (Monsanto) is washed with deionized distilled water to remove fine particles. The washed apatite is dried at 37° C. for 3 days. 200 mgs of washed hydroxyapatite are placed into each of 15 screw capped plastic tubes. To each tube, 3 ml slurries of each of the dental creams are added. The test is run is triplicate. The slurries are shaken with hydroxyapatite at 37° for 1 hour. At the end of incubation period, hydroxyapatite is centrifrigued at 5000 rpm in a Sorvall centrifuge using S34 rotor for 15 minutes. The supernatant is aspirated off and hydroxyapatite is washed with deionized distilled water similarly twice. Each treated hydroxyapatite is dissolved in 5 ml of perchloric acid in a 100 cc volumetric flask and made to 100 cc with deionized distilled water. 0.5 ml of perchloric treated hydroxyapatite is mixed with 0.5 ml of buffer to adjust the pH between 5.0 and 6.0. The ionic fluoride in hydroxyapatite is then determined via a potentiometric titeration method using ion specific electrode (Orion). The determinations are performed on five samples. 10 grams of each cream are placed in 50 ml centrifuge tubes. 20 grams of deionized distilled water are then added and mixed to slurry. The suspension is centrifuged at 12,000 rpm for 15 minutes and the supernatant is used for hydroxyapatite absorption tests.

The following amounts of fluoride are absorbed in apatite for each dental cream:

| Dental Cream | Fluoride Absorbed in Apatite with Standard Deviation |
|---|---|
| A (2.75% EDITEMPA; 0.22% NaF) | 704.1 ± 30.9 |
| B (2.75% EDITEMPA; 0.76% MFP) | 352.6 ± 18.4 |
| C (2% EDITEMPA; 0.15% NaF) | 411.36 ± 7.44 |
| D (2% EDITEMPA; 0.5% MFP) | 152.3 ± 7.44 |
| E | 31.9 ± 6.1 |

Bioavailibility of fluoride provided by sodium fluoride is significantly better than is provided by sodium monofluorophosphate when A is compared with B and C is compared with D.

EXAMPLE 3

The following dental cream is prepared in accordance with the procedure outlined in Example 1:

| | PARTS |
|---|---|
| Glycerine | 25.00 |
| Sodium carboxymethyl cellulose | 1.30 |
| Sodium benzoate | 0.50 |
| Sodium saccharine | 0.20 |
| Titanium dioxide | 0.40 |
| EDITEMPA-sodium (6-7) salt | 2.75 |
| Sodium fluoride | 0.10 |
| Zeo 49 | 29.00 |
| Sodium lauryl sulfate | 1.50 |
| Flavor | 1.00 |
| Water | Q.S. to 100 |

The mole ratio of tetra (methylene polyphosphonate) to fluoride is 3.1:1.

The presence of sodium fluoride does not reduce the anticalculus effect of a similarly prepared dental cream from which sodium fluoride is omitted.

EXAMPLE 4

Solutions B–N, below, are prepared and compared to water control (A).

Calculus inhibition by each solution is determined by a procedure based on that described in "Calculus Tissue Research", Vol. 34, pages 8–16, 1982. The tests are run 5 times at 37° C. in order to precisely simulate the environment or oral cavity. In this test the formation of hydroxyapatite is measure titrimetrically in the pH stat procedure.

$$5\ Ca^{++} + 3\ HPO_4^= + H_2O \rightarrow (\text{Precursor Phase}) \rightarrow Ca_5(PO_4)OH + 4H^+$$

The materials which inhibit this reaction are effective against calculus formation. The concentrations of the inhibitors used are substoichiometric level to that of total calcium in the reaction mixture in order to avoid a sequestration or direct chelation effect.

Water (A) is used as a control as are solutions B–E with various fluorides and no diamine tetra (methylene phosphonate) and F, a positive control, with 20 ppm of EDITEMPA sodium (6-7) salt and no fluoride. Solutions G–N each contain 20 ppm EDITEMPA sodium (6-7) salt and fluoride. The formula variations are as follows:

| CONTROLS | PPM EDITEMPA SODIUM (6-7) SALT IN SOLUTION | PPM FLUORIDE COMPOUND IN SOLUTION |
|---|---|---|
| A-Water | — | — |
| B-Sodium fluoride | — | 2.2 |
| C-Sodium monofluorophosphate | — | 7.6 |
| D-Stannous Fluoride | — | 4.0 |
| E-N',N',N'—tris (hydroxyethyl) N—octadecyl 1,3-aminopropane hydrofluoride (amine fluoride) | — | 3.44 |
| F-EDITEMPA-sodium (6-7) salt | 20 | — |

The controls B–F result in hydroxyapatite formation in the times indicated below (with standard deviations) compared to water control A.

| | Time in minutes for HA formation | Inhibition Time in Minutes Compared to Water Control A |
|---|---|---|
| A (Water) | 3.4 ± 0.5 | |
| B | 5.1 ± 0.1 | 1.7 |
| C | 3.6 ± 0.3 | 0.2 |
| D | 4.1 ± 0.5 | 0.7 |
| E | 4.6 ± 0.5 | 1.2 |
| F (Positive Control) | 19.4 ± 2.0 | 16 |

Solutions G–N contain 20 ppm of EDITEMPA-sodium (6-7) salt and fluoride as follows:

| | PPM FLUORIDE COMPOUND | MOLE RATIO TETRA (METHYLENE PHOSPHONATE) TO FLUORIDE |
|---|---|---|
| G | $2.2 \times 10^{-4}$ sodium fluoride | 0.98:1 |
| H | $1.54 \times 10^{-4}$ sodium fluoride | 1.4:1 |
| I | $7.6 \times 10^{-4}$ sodium monofluorophosphate | 0.98:1 |
| J | $5.32 \times 10^{-4}$ sodium monofluorophosphate | 1.4:1 |
| K | $4 \times 10^{-4}$ stannous fluoride | 0.98:1 |
| L | $2.8 \times 10^{-4}$ stannous fluoride | 1.4:1 |
| M | $3.44 \times 10^{-4}$ amine fluoride | 0.98:1 |
| N | $2.41 \times 10^{-4}$ amine fluoride | 1.4:1 |

The times for hydroxyapatite formation to occur (with standard deviations) and inhibition times compared to water control A and positive control F are indicated below for solutions G and H which contain sodium fluoride:

| | Time in Minutes for Hydroxyapatite Formation | Inhibition Time in minutes Compared to Water Control A | Inhibition Time in Minutes Compared to Positive Control F |
|---|---|---|---|
| G | 16.3 ± 0.8 | 12.9 | −3.1 |
| H | 19.8 ± 0.1 | 16.4 | 0.4 |

These results reveal that at a mole ratio of tetra(methylene phosphonate) to fluoride of 1.4:1 (H) with sodium fluoride as the fluoride source, calculus inhibition is optimum while at a lower mole ratio (G) calculus inhibition is less.

The times for hydroxyapatite formation to occur (with standard deviations) and inhibition times compared to water control A and positive control F are indicated below for solutions I and J with sodium monofluorophosphate; K and L with stannous fluoride; and M and N with amine fluoride:

| | Time in Minutes for Hydroxyapatite Formation | Inhibition Time in Minutes Compared to Water Control A | Inhibition Time in Minutes Compared to Positive Control F |
|---|---|---|---|
| I | 14.5 ± 0.8 | 11.1 | −4.9 |
| J | 17.3 ± 0.5 | 13.9 | −2.1 |
| K | 12.4 ± 0.7 | 9.0 | −7 |
| L | 14.0 ± 0.2 | 10.6 | −5.4 |
| M | 11.9 ± 1.2 | 8.5 | −7.5 |
| N | 13.4 ± 0.5 | 10 | −6 |

These results, further compared with the results with solution H reveal that sodium monofluorophosphate (I and J); stannous fluoride (K and L); and amine fluoride (M and N) do not provide optimum calculus inhibition as does sodium fluoride at a mole ratio of tetra (methylene phosphonate) to fluoride of 1.4:1 (H).

EXAMPLE 5

The following mouthwash is prepared by adding humectant, alcohol, preservative and nonionic surface active agent to water and then incorporating therein fluoride, surface active agent, polyamine polyphosphonate and flavor:

| | PARTS |
|---|---|
| Ethanol | 10.00 |

| | PARTS |
|---|---|
| Sodium saccharin | 0.03 |
| Glycerine | 10.00 |
| Polyoxyethylene-polyoxypropylene condensate (Pluronic F108) | 2.0 |
| EDITEMPA-sodium (6–7) salt | 0.69 |
| Sodium fluoride | 0.05 |
| Flavor | 0.22 |
| Water | 77.01 |

The mole ratio of tetra (methylene phosphonate) to fluoride is 1.4:1. The mouthwash is effective in inhibiting calculus formation and has high fluoride retention.

It will be apparent to one skilled in the art that modifications of the above examples may be made thereto.

I claim:

1. An oral composition comprising an oral vehicle, at least about 0.275% by weight of a diamine tetra (methylene phosphonate) having the formula:

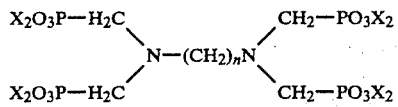

wherein n is a number from 1 to 10 and X is selected from the group consisting of hydrogen and an orally acceptable cation, at least one X group being an orally acceptable cation, and alkali metal fluoride, in amount which provides about 0.01–1% by weight of fluoride ion, the mole ratio of the tetra (methylene phosphonate) portion, $(CH_2\text{-}PO_3^{-2})_4$, of said diamine tetra (methylene phosphonate) to fluoride ion being at least about 1.4:1.

2. The oral composition claimed in claim 1 wherein said diamine tetra (methylene phosphonate) is ethylene diamine tetra (methylenephosphonic acid) sodium salt and said alkali metal fluoride is sodium fluoride.

3. The oral composition claimed in claim 1 wherein said diamine tetra (methylene phosphonate) is present in amount of about 0.275–5.5% by weight.

4. The oral composition claimed in claim 1 wherein said alkali metal fluoride is sodium fluoride, which sodium fluoride is present in amount of about 0.1–0.32% by weight.

5. The oral composition claimed in claim 1 wherein the mole ratio of said diamine tetra (methylene phosphonate) to fluoride ion is from about 1.4:1 to about 3.2:1.

6. The oral composition claimed in claim 1 wherein about 15–75% by weight of an orally acceptable dental polishing material is present and said composition is a toothpaste or dental cream or gel.

7. The oral composition claimed in claim 6 wherein said polishing material is a siliceous polishing agent.

8. The oral composition claimed in claim 1 wherein said oral vehicle contains a mixture of water and nontoxic alcohol and said composition is a mouthwash.

* * * * *

UNITED STATES PATENT AND TRADEMARK OFFICE
CERTIFICATE OF CORRECTION

PATENT NO. : 4,436,721
DATED : March 13, 1984
INVENTOR(S) : Abdul Gaffar

It is certified that error appears in the above-identified patent and that said Letters Patent are hereby corrected as shown below:

Column 3, line 30, cancel "amorphorous" and insert --amorphous--.

Column 6, line 39, cancel "and" (second occurence) and insert --on--.

Column 7, line 30, after "cream", insert --B--.

Column 7, line 44, right-hand column (under $\underline{E}$), cancel "0.50", after amount of sodium monofluorophosphate in dental cream E.

Column 8, line 22, cancel "titeration" and insert --titration--.

Signed and Sealed this

Ninth Day of October 1984

[SEAL]

Attest:

Attesting Officer

GERALD J. MOSSINGHOFF

Commissioner of Patents and Trademarks